(12) United States Patent
Han et al.

(10) Patent No.: US 6,932,604 B2
(45) Date of Patent: Aug. 23, 2005

(54) INTERPROXIMAL SQUIRT BRUSH

(76) Inventors: Johnny Steve Han, 1830 Debann Pl., Rowland Heights, CA (US) 91748; Mei-Ling Pauling Han, 1830 Debann Pl., Rowland Heights, CA (US) 91748

( * ) Notice: Subject to any disclaimer, the term of this patent is extended or adjusted under 35 U.S.C. 154(b) by 0 days.

(21) Appl. No.: 10/837,451

(22) Filed: Apr. 29, 2004

(65) Prior Publication Data

US 2005/0032020 A1 Feb. 10, 2005

Related U.S. Application Data

(63) Continuation-in-part of application No. 10/637,116, filed on Aug. 8, 2003.

(51) Int. Cl.[7] .......................... A61C 17/00; A47L 13/22
(52) U.S. Cl. ......................................... 433/80; 401/290
(58) Field of Search .......................... 433/80, 82, 215; 15/167.1, 176.1; 401/185, 28, 268, 29; 222/569, 192; 132/112

(56) References Cited

U.S. PATENT DOCUMENTS

| | | | | |
|---|---|---|---|---|
| 3,174,174 A | * | 3/1965 | Dengler | 401/25 |
| 4,828,420 A | * | 5/1989 | Otsuka et al. | 401/268 |
| 4,875,602 A | * | 10/1989 | Chickering et al. | 222/187 |
| 5,330,357 A | * | 7/1994 | Keller | 433/215 |
| 5,755,572 A | * | 5/1998 | Bab et al. | 433/80 |
| 2003/0224320 A1 | * | 12/2003 | Kandelman et al. | 433/80 |

* cited by examiner

*Primary Examiner*—Cary E. O'Connor
(74) *Attorney, Agent, or Firm*—Raymon Y. Chan; David and Raymond

(57) ABSTRACT

An interproximal squirt brush includes a solution container having a compressible solution chamber for containing a washing solution and a nozzle head having an opening, and a brush head including a brush arm and a brush member. The brush arm has a brush portion and a retention portion slidably inserted into the opening of the solution container, wherein a dispensing channel is formed between the retention portion of the brush arm and the inner wall of the nozzle head for allowing the solution to pass therethrough. The brush member is provided at the brush portion of the brush arm. Therefore, when a compression force is applied on the solution container, the solution is released to the brush member through the dispensing channel of the nozzle head.

15 Claims, 9 Drawing Sheets

INTERPROXIMAL SQUIRT BRUSH

CROSS-REFERENCE OF RELATED APPLICATION

This is a Continuation-In-Part application of a non-provisional application having an application Ser. No. 10/637,116 and a filing date of Aug. 8, 2003.

BACKGROUND OF THE PRESENT INVENTION

1. Field of Invention

The present invention relates to a dental instrument, and more particularly to an interproximal squirt brush, which can substantially clean and remove stains and food residuals between teeth and around implants by both physical therapy and chemical treatment.

2. Description of Related Arts

Gum disease (periodontitis) is one of the common dental problems. Periodontal disease, especially in the early stages, is usually not painful such that many people having gum disease do not even realize it. Researches report that the periodontal disease is an infection in the gums caused by the bacteria in plaque, wherein plaque and bacteria build up on and between the teeth. To prevent the gum disease, dentists always suggest having a better oral hygiene by brushing and flossing regularly. In addition, mouthwash is also considered as one of the effective methods for removing plaque and bacteria. By reducing the amount of plaque on your teeth, you can reduce the amount of bacteria in your mouth.

Brushing method is the most common method for removing plaque built-up on the teeth. However, due to the structure of the toothbrush, the bristles of the toothbrush cannot effectively remove the plaque from the areas between teeth and around the gums. Therefore, flossing becomes the effective way to help the user to remove plaque and debris from between the teeth, especially the areas inaccessible to the toothbrush. It is ideal to use the mouthwash after brushing and/or flossing since the mouthwash with medicament is capable of not only effectively removing oral bacteria and stain on the teeth but also reducing bad breath.

However, the flossing technique of holding the floss by hand leads to different operational result depending on the users. Flossing requires the user to floss up, down, right, left, front, and back. This six-step process is too cumbersome and time consuming. Therefore, the conventional floss is disadvantageous in practical use. An improved toothpick, which combines the advantages of both toothbrush, floss, and mouthwash, comprises a brush head having a size adapted to fit between the teeth and gum line to brush the areas thereof. Due to the friction between the brush head and the gum line, tenderness during dry brushing always gives discomfort to the user. An improper brushing the gum line may even cause the gum bleeding.

SUMMARY OF THE PRESENT INVENTION

The main object of the present invention is to provide an interproximal squirt brush for substantially cleaning and removing stains and/or food residuals between teeth and around implants by both physical therapy and chemical treatment.

Another object of the present invention is to provide an interproximal squirt brush, wherein a user is able to use the interproximal squirt brush with mouthwash, which combines the flossing and mouthwash techniques, in one step to remove oral bacteria between the gums and teeth, stain and plaque built on the teeth, and to reduce bad breath at the same time.

Another object of the present invention is to provide an interproximal squirt brush, wherein the solution is guided to apply on the brush head such that when the brush head fits between the teeth and gum line during brushing process, the solution not only penetrates through the area between the teeth and around the gum line to remove the stain and bad breath, but also functions as a lubricant to minimize the friction between the brush member and the gum line so as to prevent gum bleed and uncomfortable feeling to the user. In other words, the solution, such as medicament, can be used for the present invention to control infection between the gums thus preventing the growth of gum disease.

Another object of the present invention is to provide an interproximal squirt brush, wherein the brush head has a retention portion inserted into an opening of the solution container to retain the brush head in position such that the solution contained in the solution container can be substantially applied on the brush head by a compression force applied on the solution container. Accordingly, there are additional shapes, animal characters, and sizes for the solution container that can be attached to the brush head, such as the elongating and shrinking brush end.

Another object of the present invention is to provide an interproximal squirt brush, wherein the cleaning operation is easy and simple by fitting the brush head between the teeth and around gum line to brush therewith and by squeezing the solution towards the brush head.

Another object of the present invention is to provide an interproximal squirt brush, wherein not only the brush head is replaceably mounted to the solution container but also the solution can be refilled into the solution container so as to extend the service life span of the interproximal squirt brush of the present invention. For example, the solution can be easily replaced by removing a rubber stopper at the bottom of the solution container.

Another object of the present invention is to provide an interproximal squirt brush, wherein no expensive or complicated structure is required to employ in the present invention in order to achieve the above mentioned objects. Therefore, the present invention successfully provides an economic and efficient solution not only for removing plaque and stain on the teeth through the flossing technique but also for reducing oral bacteria and bad breath through the mouthwash technique.

Accordingly, in order to accomplish the above objects, the present invention provides an interproximal squirt brush, comprising:

a solution container comprising a compressible container body having a compressible solution chamber for containing a solution and a nozzle head having an opening communicating with the compressible solution chamber and being extended from the container body; and a brush head, comprising:

an elongated brush arm having a brush portion and a retention portion connected to the nozzle head to hold the brush arm in position, wherein a dispensing channel is provided at the nozzle head adjacent to the retention portion of the brush arm to deliver the solution from the container body to the brush portion of the brush arm through the nozzle head; and a brush member provided at the brush portion of the brush arm, thereby when a compression force is applied on the container body, the solution is released to deliver to the brush member through the dispensing channel of the nozzle head.

These and other objectives, features, and advantages of the present invention will become apparent from the fol-

DETAILED DESCRIPTION OF THE PREFERRED EMBODIMENT

Figure 1:
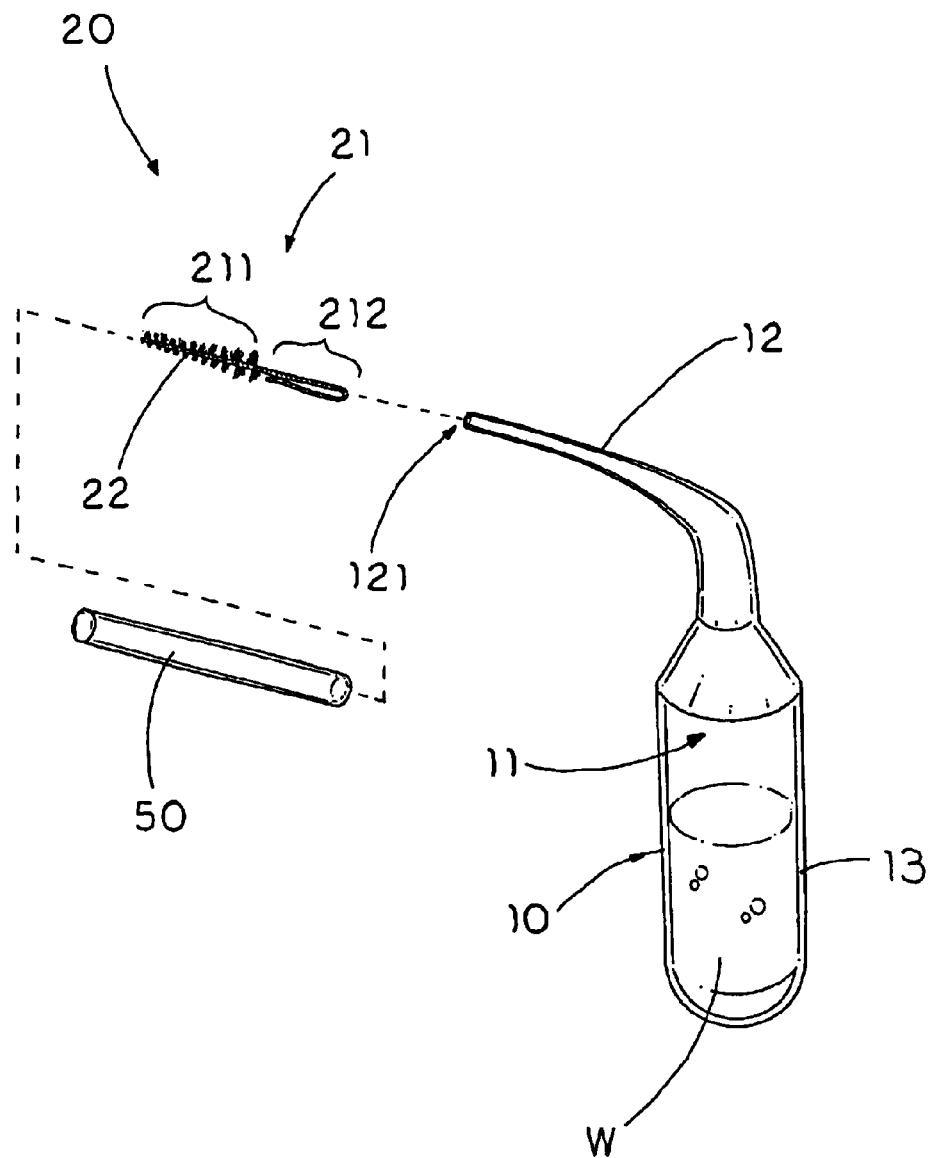
FIG. 1 is a perspective view of an interproximal squirt brush according to a preferred embodiment of the present invention.
Figure 2:
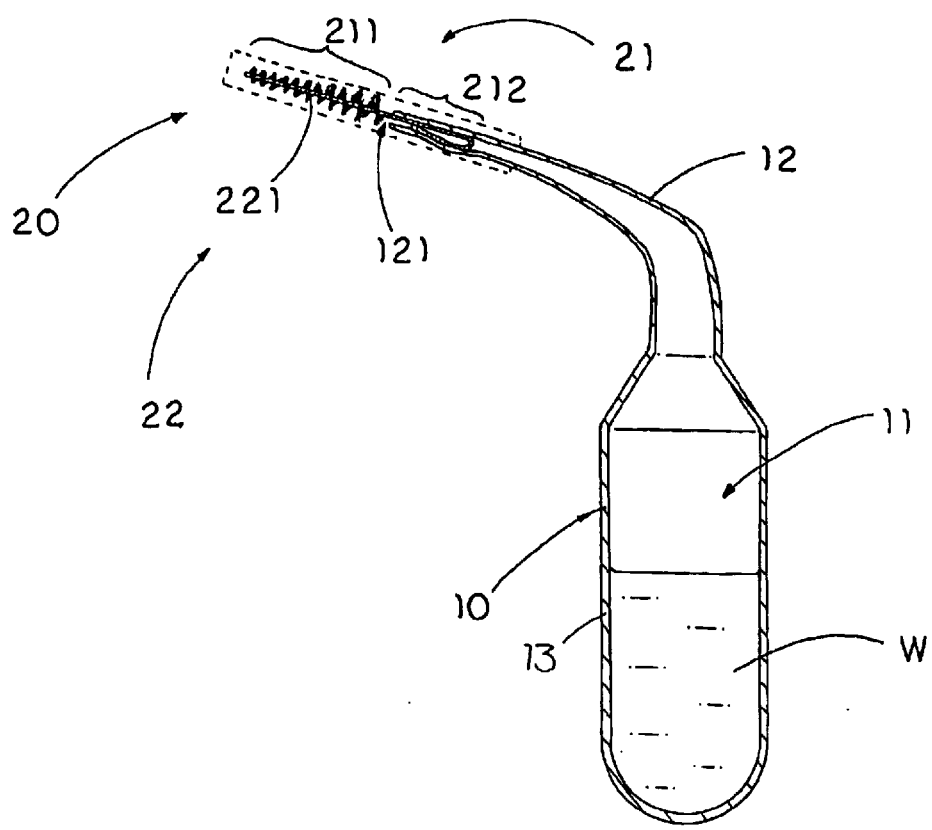
FIG. 2 is a side sectional view of the interproximal squirt brush according to the above preferred embodiment of the present invention.
Figure 3:
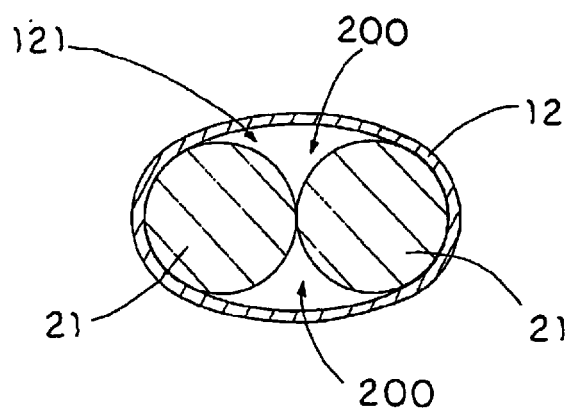
FIG. 3 is a front sectional view of the interproximal squirt brush according to the above preferred embodiment of the present invention.

Referring to FIGS. 1 through 3 of the drawings, an interproximal squirt brush according to a preferred embodiment of the present invention is illustrated, wherein the interproximal squirt brush comprises a solution container 10 and a brush head 20 comprising an elongated brush arm 21 and a brush member 22.

The solution container 10 comprises a compressible container body 13 having a compressible solution chamber 11 defined therein for containing a solution W, such as a washing solution or a cleansing solution, and a nozzle head 12 having an opening 121 communicating with the compressible solution chamber 11.

The brush arm 21 of the brush head 20 has a brush portion 211 and a retention portion 212 connected to the nozzle head 20 to hold the brush arm 21 in position, wherein a dispensing channel 200 is provided at the nozzle head 12 adjacent to the retention portion 212 to deliver the solution W from the container body 13 formed between the retention portion 212 of the brush arm 21 and the inner wall of the nozzle head 12 for allowing the solution W to deliver towards the brush portion 211 of the brush arm 21 through the nozzle head 12.

According to the preferred embodiment of the present invention, the retention portion 212 is inserted into the opening 121 of the solution container 10 for providing an urging force as a locking force against an inner wall of the nozzle head 12 in order to hold the brush arm 21 in position. The dispensing channel 200 is formed between the retention portion 212 of the brush arm 21 and the inner wall of the nozzle head 12 to allow the solution W to pass towards the brush portion 211 of the brush arm 21 through the nozzle head 12.

The brush member 22 is provided at the brush portion 211 of the brush arm 21, thereby when a compression force is applied on the container body 13, the solution W is released to deliver to the brush member 22 through the dispensing channel 200 of the nozzle head 12.

According to the preferred embodiment, the container body 13 is preferably made of plastic such that a user is able to squeeze the solution container 13 to compress the compressible solution chamber 11 to dispense the solution W therein through the opening 121 of the nozzle head 12. The nozzle head 12 is made to have a supportive and rigid structure to substantially support the brush head 20 so as to prevent the nozzle head 12 from being bent when the brush head 20 fits between the teeth during the brushing operation. Accordingly, the nozzle head 12 is integrally extended from the solution container 13 to communicate with the compressible solution chamber 11. The solution container 10 is embodied as a one-piece integral member adapted to be made by injection molding techniques, so as to minimize the manufacturing cost of the interproximal squirt brush of the present invention.

Accordingly, the solution W can be water or medicament commonly sold in market for removing oral bacteria and bad breath. It is worth to mention that the user is able to squeeze the solution container 10 to suck the solution W into the compressible solution chamber 11 to refill the solution W.

The brush head 20, according to the preferred embodiment, is an interproximal brush arranged to fit between the teeth and around the gum line of the user so as to clean the teeth and massage the gum. As shown in FIG. 1, the brush head 20 is replaceably mounted to the solution container 10 such that the user is able to replace the used brush head 20 from the solution container 10 with a new brush head 20 by inserting the brush head 20 into the opening 121 of the solution container 10.

The brush arm 21, which is made of bendable material such as metal wire, is a wiring arm wherein the retention portion 212 of the brush arm 21, having a loop shaped, is formed by bending a tail portion of the wiring arm to form a U-shaped structure in such a manner that when the retention portion 212 of the brush arm 21 is slidably inserted into the opening 121 of the solution container 10, the retention portion 212 of the brush arm 21 is arranged to bias against the inner wall of the nozzle head 12 so as to hold the brush head 20 in position, as shown in FIG. 2.

As shown in FIG. 3, a diameter of the opening 121 is slightly smaller than a width of the retention portion 212 of the brush arm 21 such that when the retention portion 212 of the brush arm 21 is inserted into the opening 121 of the solution container 10, the retention portion 212 of the brush arm 21 biases against the inner wall of the nozzle head 12 to slightly deform a shape of the nozzle head 12. In other words, the retention portion 212 of the brush arm 21 provides the urging force as the locking force to securely retain the brush head 20 in position.

In addition, the dispensing channel 200 is the clearance formed between the retention portion 212 of the brush arm 21 and the inner wall of the nozzle head 12 wherein the dispensing channel 200 is capable of allowing the solution W passing therethrough towards the brush portion 211 of the brush arm 21.

The brush member 22, according to the preferred embodiment, comprises a plurality of wire bristles 221 radially extended from the brush portion 211 of the brush arm 21 for fitting between the teeth and around the gum line to perform the brushing and/or flossing action so as to remove the stain and plaque on the teeth, as shown in FIG. 1. In addition, when the compression force is applied on the solution container 10, the solution W is delivered to the wire bristles 221 of the brush member 22 through the dispensing channel 200 of the nozzle head 12. Therefore, when the brush member 22 fits between the teeth and gum line during brushing process, the solution W not only penetrates through the area between the teeth and around the gum line to remove the stain and bad breath, but also functions as a lubricant to minimize the friction between the brush member 22 and the gum line so as to control gum disease and reduce uncomfortable feeling to the user.

It is worth to mention that when the brush member 22 fits between the teeth or around the gum line, the opening 121 of the nozzle head 12 is guided to point at the gap between the teeth or the gum line. Therefore, the user is able to precisely deliver the solution W towards the gap between the teeth and/or the gum while the brush member 22 is located.

As shown in FIG. 1, the interproximal squirt brush further comprises a tubular protective cap 50 having a predetermined length to receive the brush head 20 therein wherein the nozzle head 12 is slidably inserted into the protective cap 50 so as to protectively cover the brush head 20 within the protective cap 50.

Figure 4:
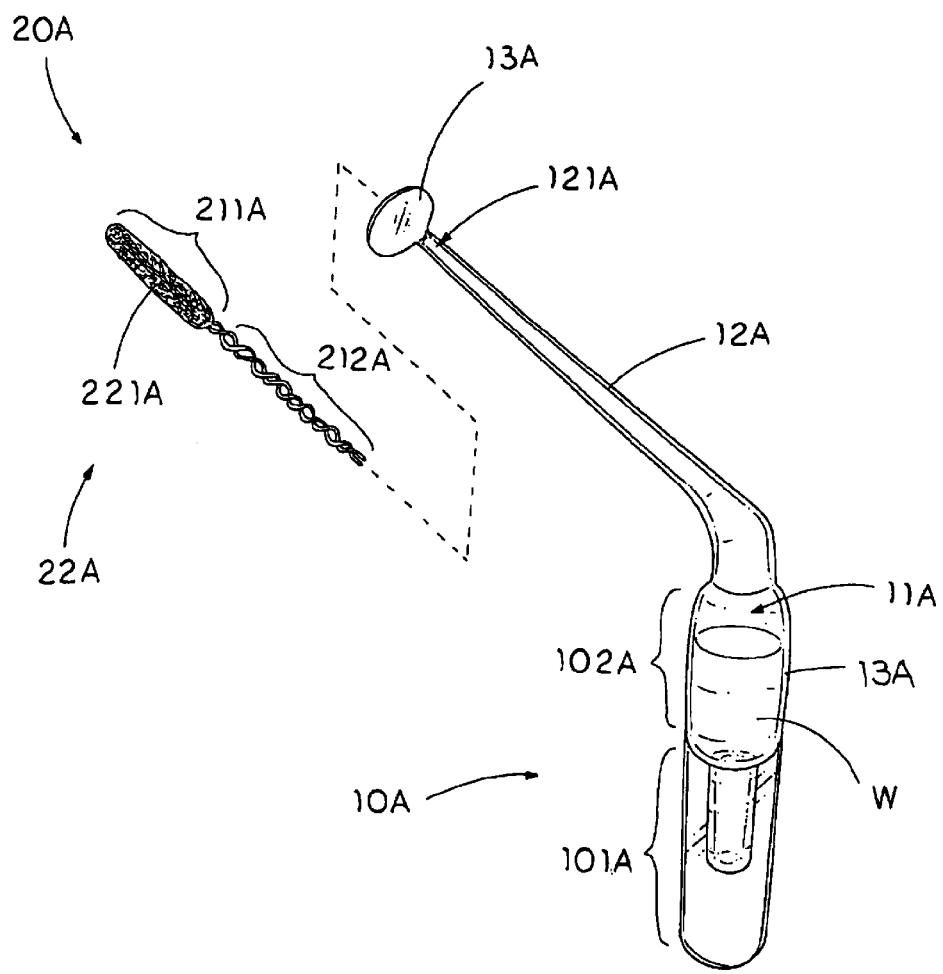
FIG. 4 illustrates a first alternative mode of a brush head of the interproximal squirt brush according to the above preferred embodiment of the present invention.

FIG. 4 illustrates a first alternative mode of the brush head 20A which comprises the brush arm 21A having the retention portion 212A inserted into the opening 121A of the solution container 10A, and the brush member 22A provided at the brush portion 211A of the brush arm 21A.

Alternatively, the solution container 13A of the solution container 10A has a handle portion 101A and a squeezing portion 102A, as shown in FIG. 4, wherein the solution container 10A further includes a sealing cap 13A sealedly provided at the opening 121A of the solution container 10A for retaining a predetermined volume of solution W in the compressible solution chamber 11A. Therefore, the user is able to tear off the sealing cap 13A and insert the retention portion 212A of the brush head 20A into the opening 121A of the solution container 10A. In other words, the interproximal squirt brush is well suit for disposable one-time use.

The brush arm 21A, which is made of bendable material such as metal wire, is a wiring arm wherein the retention portion 212A of the brush arm 21A is formed by bending a tail portion of the wiring arm to form a U-shaped structure and then twisting the tail portion of the wiring arm in continuous "8" shaped in such a manner that when the retention portion 212A of the brush arm 21A is slidably inserted into the opening 121A of the solution container 10A, the retention portion 212A of the brush arm 21A is arranged to bias against the inner wall of the nozzle head 12A so as to hold the brush head 20A in position, as shown in FIG. 4.

The brush member 22A comprises a scrub element 221A attached around the brush portion 211A of the brush arm 21A, as shown in FIG. 4, wherein the scrub element 221A is a fibrous material such as nylon, polyurethane foam or polyolefins. In other words, the solution W is delivered to the scrub element 221A of the brush member 22A to clean the teeth and enhance the scrubbing process.

Figure 5:
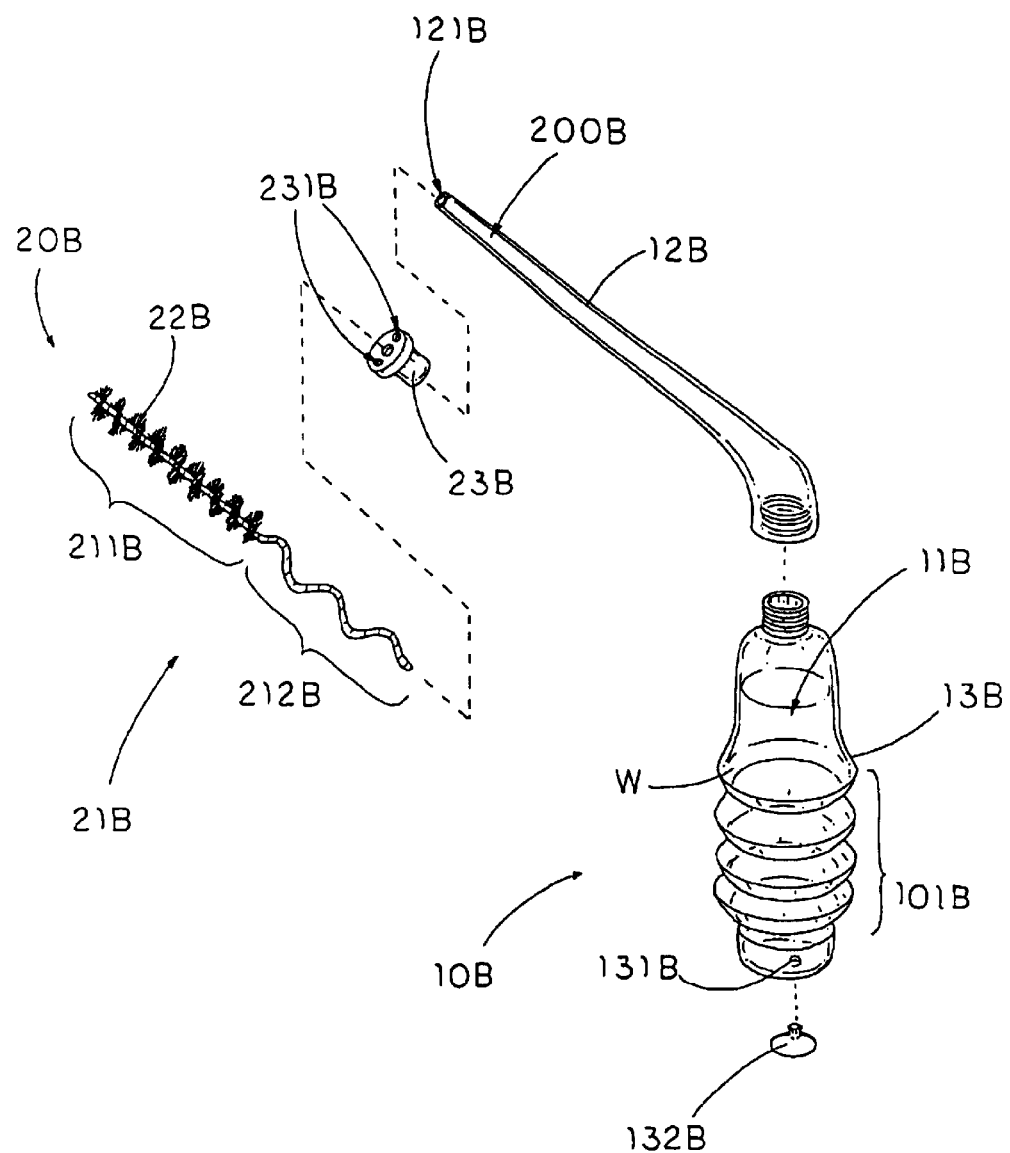
FIG. 5 illustrates a second alternative mode of the brush head of the interproximal squirt brush according to the above preferred embodiment of the present invention.

FIG. 5 illustrates a second alternative mode of the interproximal squirt brush wherein the brush arm 21B of the brush head 20B has the retention portion 212B inserted into the opening 121B of the solution container 10B and the brush portion 211B where the brush member 22B is provided thereon.

The brush arm 21B, which is made of bendable material such as metal wire, is a wiring arm, wherein the retention portion 212B of the brush arm 21B is formed by bending a tail portion of the wiring arm into in S manner so that when the retention portion 212B of the brush arm 21B is inserted into the opening 121B of the solution container 10B, the retention portion 212B of the brush arm 21B is arranged to bias against the inner wall of the nozzle head 12B so as to hold the brush head 20B in position, as shown in FIG. 5.

The solution container 10B comprises the container body 13B defining the compressible solution chamber 11B therein, wherein the nozzle head 12B is detachably attached to the container body 13B to communicate the opening 121B of the nozzle head 12B with the compressible solution chamber 11B. As shown in FIG. 5, the container body 13B has a threaded portion formed at an opening portion of the container body 13B and the nozzle head 12B has a corresponding threaded portion rotatably engaged with the threaded portion of the container body 13B so as to detachably attach the nozzle head 12B to the container body 13B for delivering the solution W from the compressible solution chamber 11B to the opening 121B of the nozzle head 12B.

In addition, the container body 13B further has a squeezable accordion style handle portion 101B that is allowed to be squeezed for compressing the solution W from the compressible solution chamber 11B to the opening 121B of the nozzle head 12B. In other words, the solution container 10B can be made of any shape and size that can be squeezed for dispensing the solution W. The container body 13B further has a refilling opening 131B formed at a bottom side thereof and comprises a rubber made stopper 132B detachably mounted to the container body 13B at the refilling opening 131B in such a manner that the solution W can be refilled into the compressible solution chamber 11B through the refilling opening 131B when the stopper 132B is detached therefrom.

It is worth to mention that the brush head 20B can be permanently attached to the nozzle head 12B while the nozzle head 12B is detachably attached to the container body 13B. In other words, the replacement of the brush head 20B is easily replaced by a new nozzle head 12B with a new brush head 20B as a whole to the container body 13B.

As shown in FIG. 5, the brush head 20B further comprises a liquid guider 23B which has at least a dispensing hole 231B and is mounted on the brush arm 21B, wherein when the retention portion 212B is inserted into the nozzle head 12B, the liquid guider 23B is attached to the opening 121B of the nozzle 12B for delivering the solution W from the compressible solution chamber 11B to outside through the dispensing hole 231B. Accordingly, when the compression force is applied on the solution container 10B, the solution W is released not only towards the brush member 22B at a position between the teeth through the dispensing channel 200B but also towards the gum around the brush member 22B through the dispensing hole 231B of the liquid guider 23B. In other words, the area in the oral cavity to be washed can be substantially increased by the liquid guider 23B.

Figure 6:
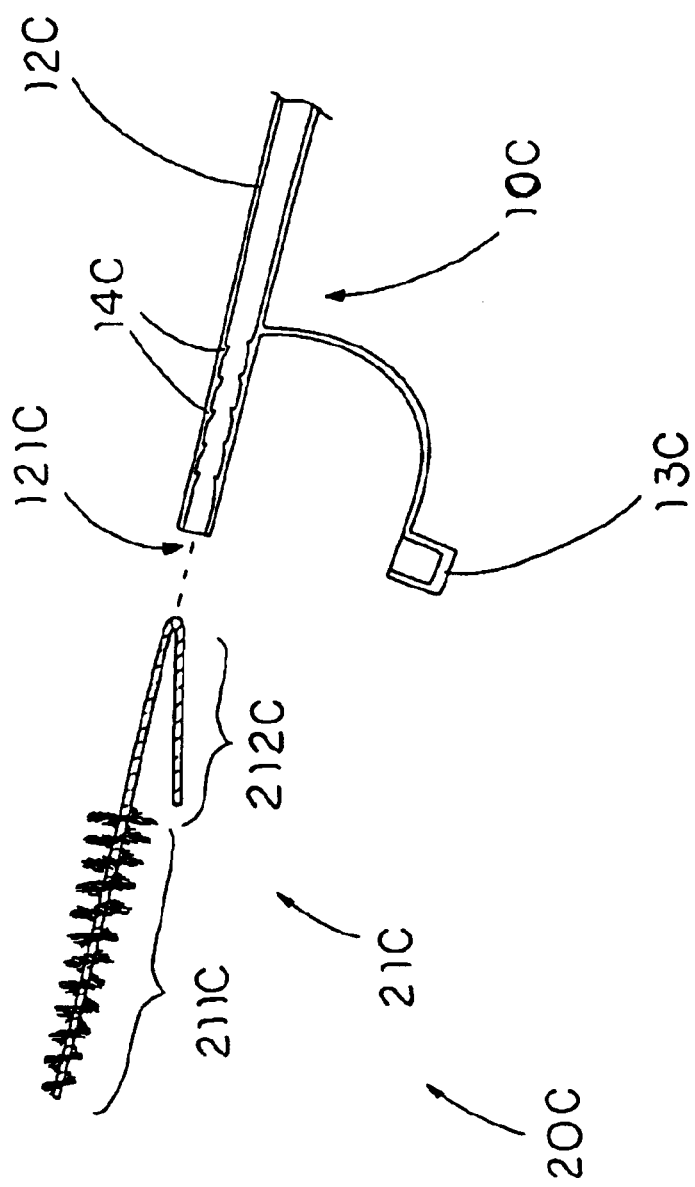
FIG. 6 illustrates a third alternative mode of the brush head of the interproximal squirt brush according to the above preferred embodiment of the present invention.

FIG. 6 illustrates a third alternative mode of the brush head 20C wherein the brush arm 21C has the retention portion 212C inserted into the opening 121C of the solution container 10C and the brush portion 211C where the brush member 22C is provided thereon.

The brush arm 21C, which is made of bendable material such as metal wire, is a wiring arm wherein the retention portion 212C of the brush arm 21B is formed by bending a tail portion of the wiring arm into a V-shaped manner in such a manner that when the retention portion 212C of the brush arm 21C is inserted into the opening 121C of the solution container 10C, the retention portion 212C of the brush arm 21C is arranged to bias against the inner wall of the nozzle head 12C so as to hold the brush head 20C in position, as shown in FIG. 6.

The solution container 10C further has at least a locking latch 14C integrally protruded from the inner wall of the nozzle head 12C to engage with the retention portion 212C of the brush arm 21C so as to lock up the brush member 22C at the opening 121C of the solution container 10C. Accordingly, in order to lock up the brush head 20C with the solution container 10C, the retention portion 212C of the brush arm 21C is inserted into the nozzle head 12C of the solution container 10C until a free end of the wiring arm of the brush arm 21C is biased against the locking latch 14C of the nozzle head 12C so as to block the brush head 20C from sliding out of the nozzle head 12C. For removing the brush head 20C from the solution container 10C, the user is able to apply a compression force on the nozzle head 12C until the free end of the wiring arm is moved offset to the locking latch 14C such that the user is able to slide the brush head 20C out of the nozzle head 12C.

In addition, a covering cap 13C can be used to detachably cover on the opening 121C of the nozzle head 12C such that the solution container 10C can be re-used to refill the solution W therein.

It is worth to mention that the interlocking configuration of the solution container 10C having the locking latch 14C can be also used for the brush head 20, 20A as shown in FIGS. 1 and 4 in addition to any other brush head products.

In view of above, the alternative modes of the solution containers 10, 10A, the brush head 20, 20A, 20B, 20C, and the liquid guider 23B can be interchanged to fit the use of the user. The size of the interproximal squirt brush of the present invention is relative small that can be stored and packed in luggage for travel or taken daily on one's person, in a handbag, or in a backpack in case of an emergency wherein one must clean one's teeth.

Figure 7:
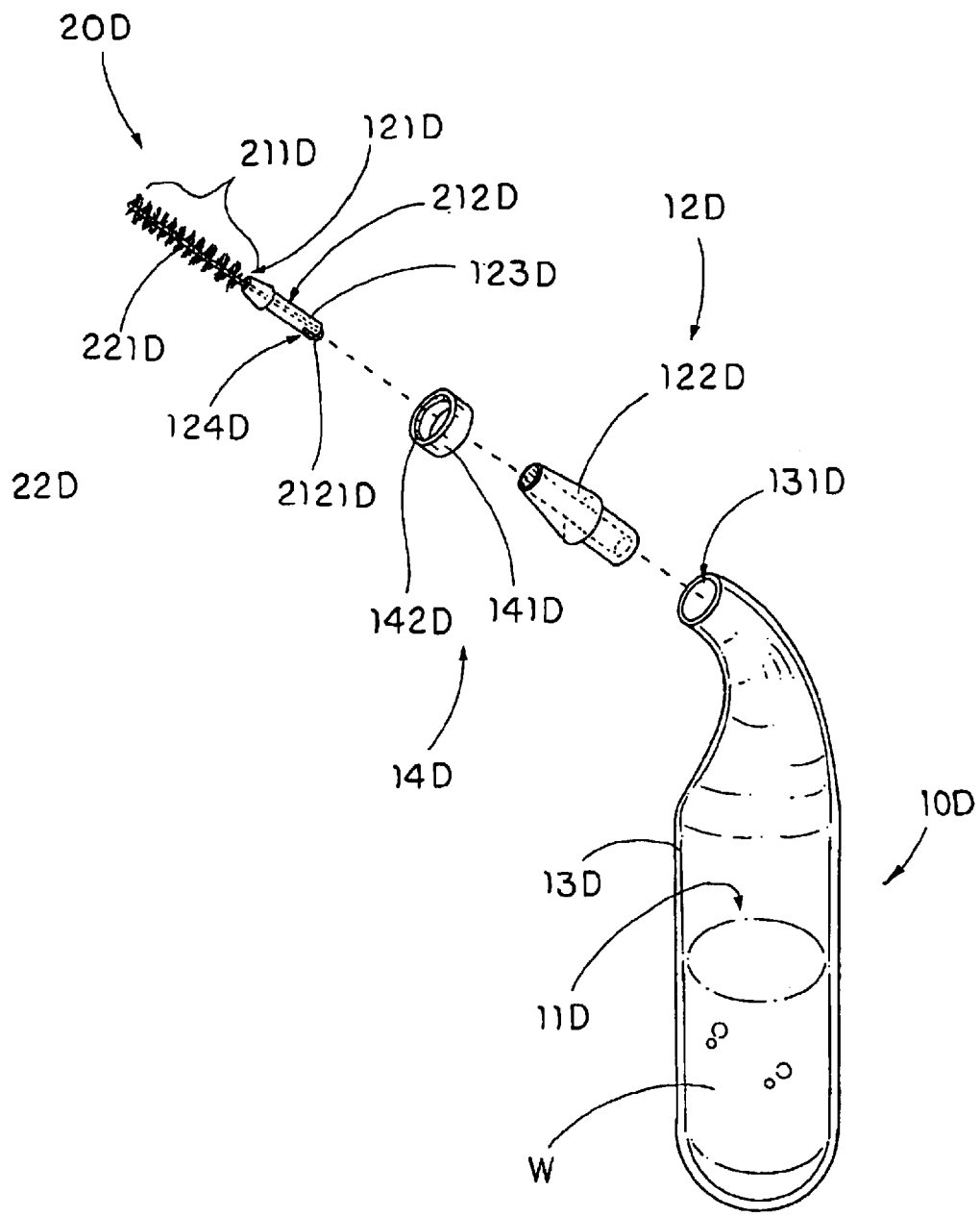
FIG. 7 is an exploded perspective view of an interproximal squirt brush according to a second preferred embodiment of the present invention.

As shown in FIG. 7, an interproximal squirt brush according to a second embodiment illustrates an alternative mode of the first embodiment of the present invention, wherein the interproximal squirt brush comprises a solution container 10D and a brush head 20D comprising an elongated brush arm 21D and a brush member 22D.

The solution container 10D comprises a container body 13D defining a compressible solution chamber 11D therein for containing a solution W and a nozzle head 12D having an opening 121D communicating with the compressible solution chamber 11D and being extended from the container body 13D.

The brush arm 21D of the brush head 20D has a brush portion 211D and a retention portion 212D inserted into the opening 121D of the solution container 10D to hold the brush arm 21D in position, wherein a dispensing channel 200D is formed between the retention portion 212D of the brush arm 21D and an inner wall of the nozzle head 12D for allowing the solution W to pass towards the brush portion 211D of the brush arm 21D through the nozzle head 12D.

The brush member 22D is provided at the brush portion 211D of the brush arm 21D. Thereby, when a compression force is applied to squeeze on the solution container 10D, the solution W is released to deliver to the brush member 22D through the dispensing channel 200D of the nozzle head 12D.

According to the second embodiment, the container body 13D is preferably made of plastic such that a user is able to compress the container body 13D to dispense the solution W in the compressible solution chamber 11D through the opening 121D of the nozzle head 12D. As shown in FIG. 7, the nozzle head 12D is detachably mounted to the container body 13D that the nozzle head 12D is replaceable.

The nozzle head 12D comprises a tubular nozzle base 122D detachably mounted to an opening portion 131D of the container body 13D and a tubular brush holder 123D coaxially mounted to the nozzle base 122D wherein the retention portion 212D of the brush arm 21D is held by the brush holder 123D so as to retain the brush head 20D in position.

Figure 8:
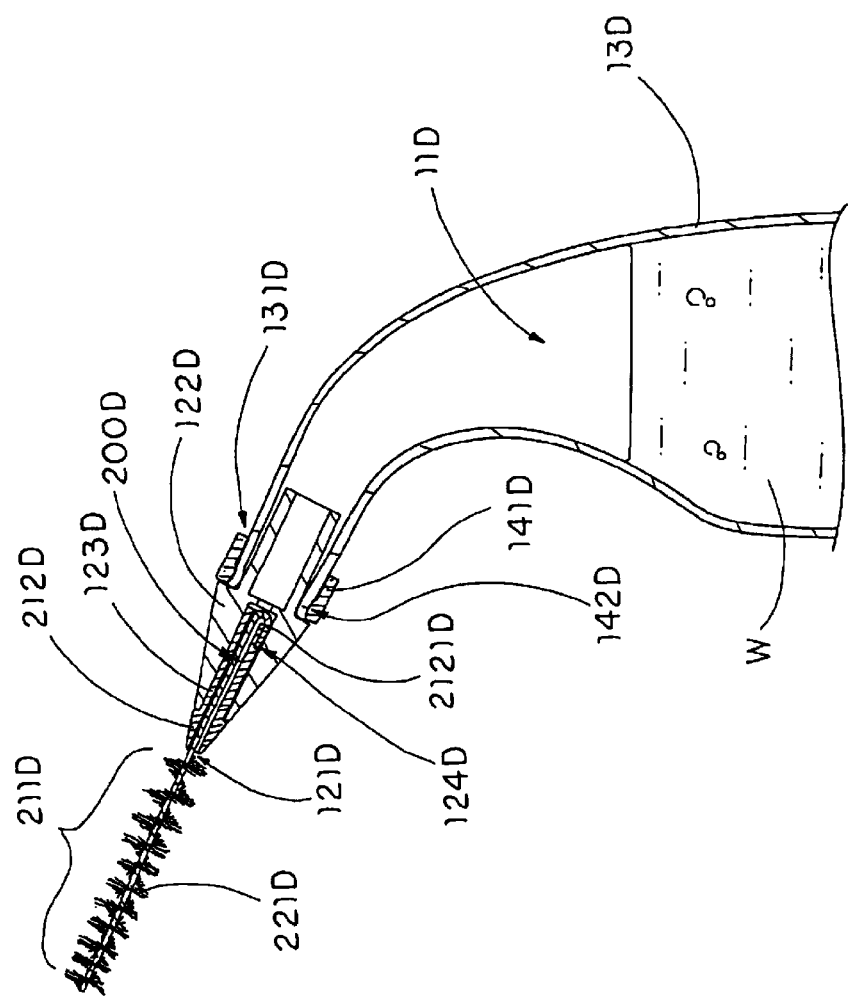
FIG. 8 is a partially sectional view of the interproximal squirt brush according to the above second preferred embodiment of the present invention.

As shown in FIGS. 7 and 8, the brush arm 21D is made of bendable material such as metal wire. The retention portion 212D of the brush arm 21D, which is embodied as the retention portion 212 of the brush arm 21 according to the first embodiment, is slidably inserted into the brush holder 123D of the nozzle head 12D, wherein the retention portion 212D of the brush arm 21D is inserted into the opening 121D of the brush holder 123D in such a manner that at least a dispensing channel 200D is formed as between the retention portion 212D of the brush arm 21D and the inner wall of the brush holder 123D of the nozzle head 12D so as to allow the solution W to pass through the dispensing channel 200D towards the brush portion 211D of the brush arm 21D.

A length of the retention portion 212D is longer than that of the brush holder 123D such that when the retention portion 212D of the brush arm 21D is inserted through the brush holder 123D, an outward extending tail 2121D of the retention portion 212D can be bent frontwardly to form a U-shape structure at a rear edge end of the brush arm 21D so as to securely hold the brush arm 21D at the brush holder 123D. In other words, the outward extending tail 2121D is bent to form the U-shape structure from an inner wall of the brush holder 123D to an outer wall thereof.

Accordingly, a guiding slot 124D is formed at the brush holder 123D wherein the guiding slot 124D is extended from the rear edge end of the brush holder 123D such that when the outward extending tail 2121D of the retention portion 212D of the brush arm 21D is bent towards the brush portion 211D, the outward extending tail 2121D of the retention portion 212D is guided to receive at the guiding slot 124D.

The brush member 22D comprises a plurality of wire bristles 221D radially and spacedly extended along the brush portion 211D of the brush arm 21D for fitting between the teeth and around the gum line to perform the brushing and/or flossing action so as to remove the stain and plaque on the teeth and the food residuals between teeth. Therefore, when the compression force is applied to squeeze on the container body 13D, the solution W is delivered to the wire bristles 221D of the brush member 22D through the dispensing channel 200D of the nozzle head 12D. Alternatively, the brush member 22D comprises a scrub element attached around the brush portion 211D of the brush arm 21D, as shown in FIG. 4.

The solution container 10D further comprises a sealing locker 14D coaxially mounted to the container body 13D to sealedly lock up the nozzle base 122D at the opening portion 131D of the container body 13D, wherein the sealing locker 14D comprises a locker ring 141D fittingly mounted around the opening portion 131D of the container body 13D to substantially hold the nozzle base 122d position and a sealing rim 142D coaxially and inwardly protruded from an edge of the locker ring 141D to tightly and sealedly bias against the opening portion 131D of the container body 13D so as to prevent the solution W from leaking at the opening portion 131D when the compression force is applied on the solution container 10 to deliver the solution W to the brush member 22D through the nozzle head 12D.

Figure 9:
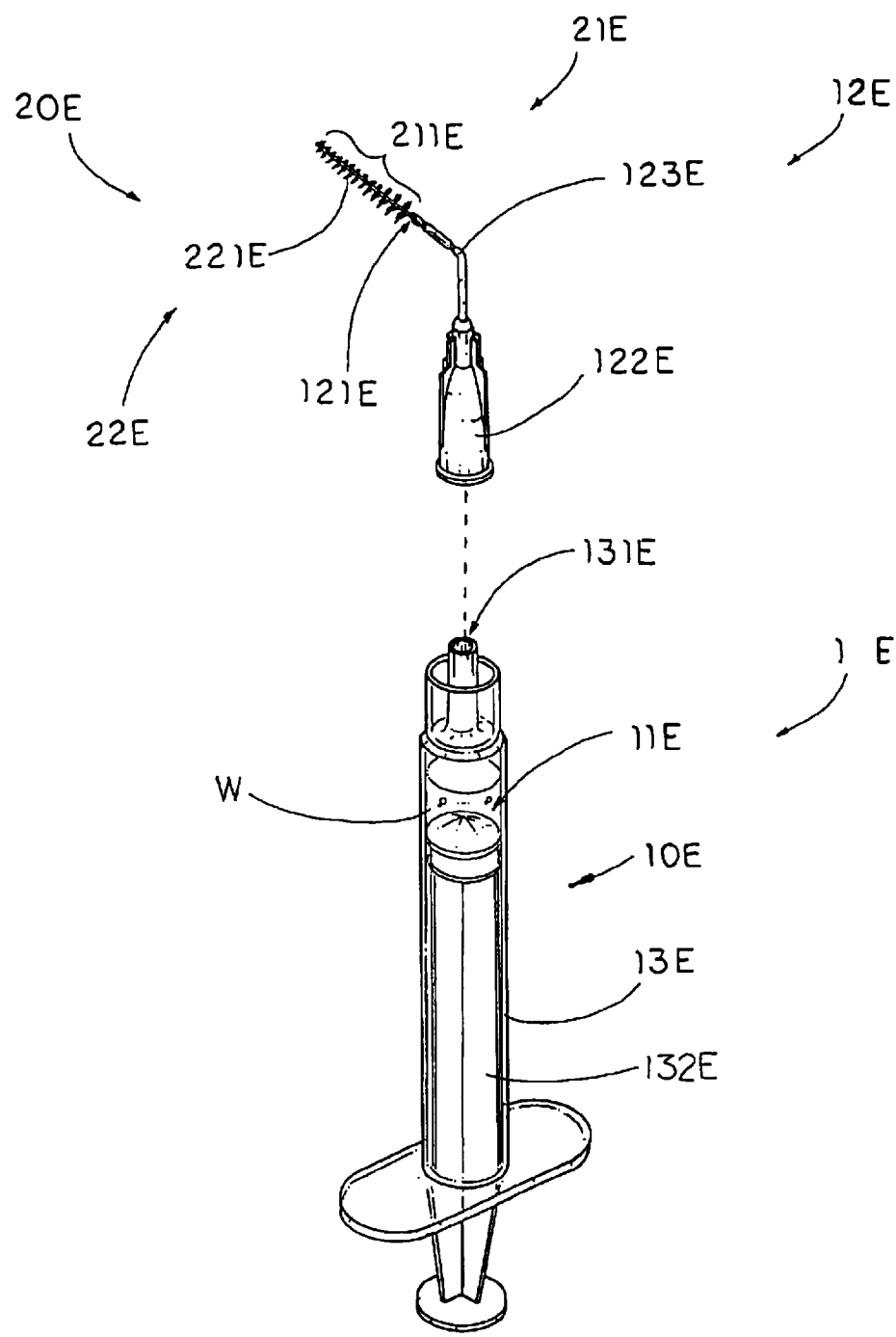
FIG. 9 is an exploded perspective view of an interproximal squirt brush according to a third preferred embodiment of the present invention.

As shown in FIG. 9, an interproximal squirt brush according to a third embodiment illustrates an alternative mode of the second embodiment of the present invention, wherein the interproximal squirt brush comprises a solution container 10E and a brush head 20E comprising an elongated brush arm 21E and a brush member 22E.

The solution container 10E comprises a container body 13E having a compressible solution chamber 11E for containing a solution W and a nozzle head 12E having an opening 121E communicating with the compressible solution chamber 11E and being extended from the container body 13E.

The brush arm 21E of the brush head 20E has a brush portion 211E and a retention portion 212E inserted into the opening 121E of the solution container 10E to hold the brush arm 21E in position, wherein a dispensing channel 200E is formed between the retention portion 212E of the brush arm 21E and an inner wall of the nozzle head 12E for allowing the solution W to deliver to the brush portion 211E of the brush arm 21E through the nozzle head 12E.

The brush member 22E is provided at the brush portion 211E of the brush arm 21E, thereby when a compression force is applied on the container body 13E, the solution W is released to deliver to the brush member 22E through the dispensing channel 200E of the nozzle head 12E. The brush member 22E comprises a plurality of wire bristles 221E radially and spacedly extended along the brush portion 211E of the brush arm 21E for fitting between the teeth and around the gum line to perform the brushing and/or flossing action so as to remove the stain and plaque on the teeth or the food residuals between teeth. Therefore, when the compression force is applied on the container body 13E by pushing in a piston member 132E inserted in said container body 13E, the solution W is pressed to deliver to the wire bristles 221E of the brush member 22E through the dispensing channel 200E of the nozzle head 12E. Alternatively, the brush member 22E comprises a scrub element attached around the brush portion 21E of the brush arm 21E, as shown in FIG. 4.

According to the third embodiment, the container body 13E is embodied as a syringe body that further has an opening portion 131E provided at a front end and is adapted for drawing the solution W in the compressible solution chamber 11E through the opening portion 131E by suction and squeezing the solution W out from the compressible solution chamber 11E in a fine steam through the nozzle head 12E, wherein the nozzle head 12E is detachably mounted to the container body 13E at the opening portion 131E thereof.

The nozzle head 12E comprises a tubular nozzle base 122E detachably mounted to the opening portion 131E of the container body 13E and a tubular brush holder 123E coaxially extended from the nozzle base 122E wherein the retention portion 212E of the brush arm 21E is held by the brush holder 123E so as to retain the brush head 20E in position.

Figure 10:
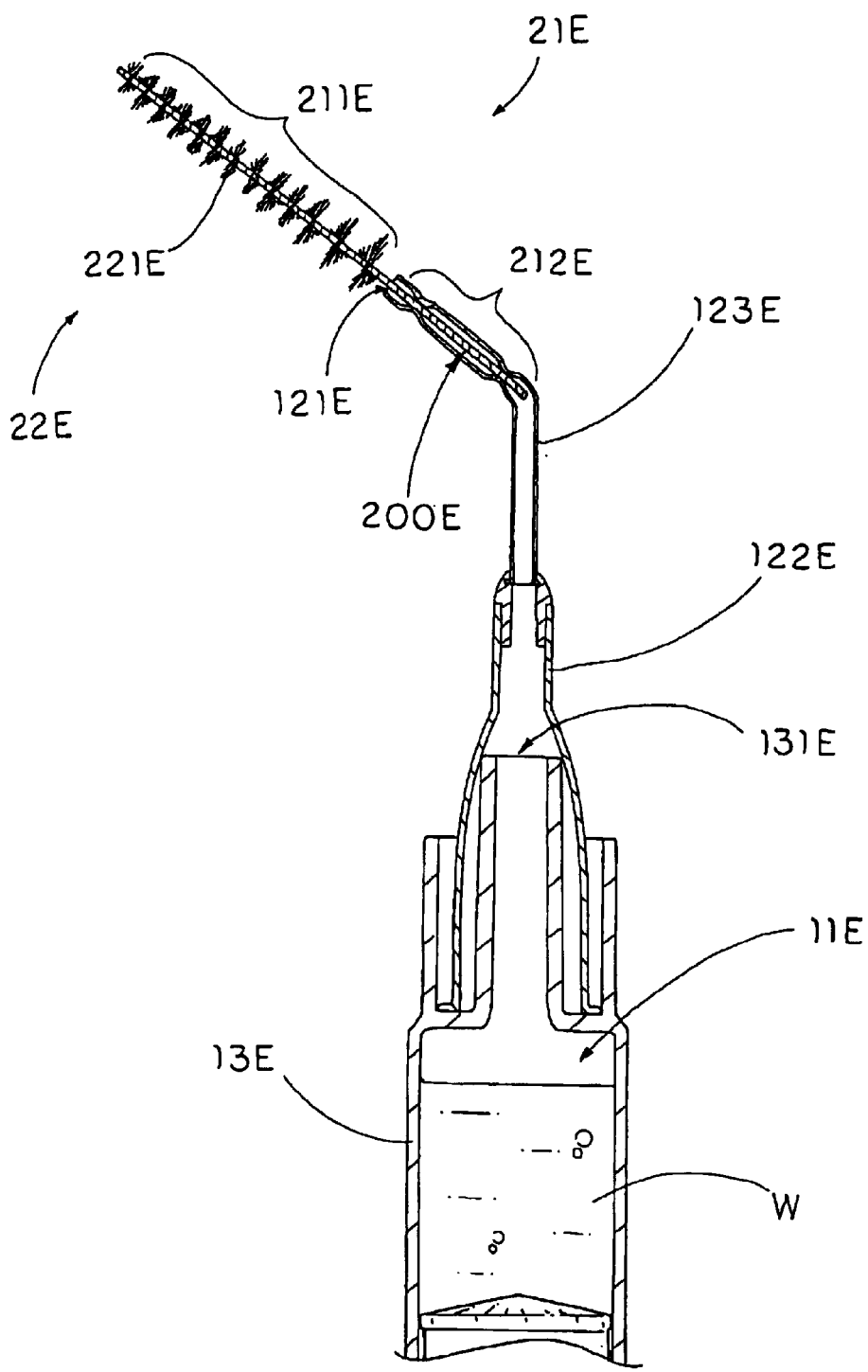
FIG. 10 is a partially sectional view of the interproximal squirt brush according to the above third preferred embodiment of the present invention.

As shown in FIGS. 9 and 10, the brush arm 21E is made of rigid material such as metal wire. The retention portion 212E of the brush arm 21E is slidably inserted into the brush holder 123E of the nozzle head 12E. According to the third embodiment, at least a portion of the brush holder 123E is flattened to sandwich the retention portion 212E of the brush arm 21E therewithin to substantially hold the brush arm 21E in position wherein the dispensing channel 200E is a clearance remained between the retention portion 212E of the brush arm 21E and the inner wall at the flattened portion of the brush holder 123E of the nozzle head 12E.

In addition, the brush holder 123E has a front portion to hold the retention portion 212E of the brush arm 21E in position and a rear portion extended from the nozzle base 122E, wherein the front portion of the brush holder 123E is inclinedly extended from the rear portion thereof such that the brush head 20E is extended at an slanted position with respect to the solution container 10E. In other words, the brush holder 123E is bent at a predetermined angle that the brush head 20E is extended at a slanted position with respect to the solution container 10E. Therefore, the inclination of the brush head 20E with respect to the solution container 10E enhances the practical use of the interproximal squirt brush of the present invention.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change in both structure and application without departure form such principles, for example the interproximal squirt brush of the present invention can also be used in cosmetic application or facial treatment. Therefore, this invention includes all modifications encompassed within the spirit and scope of the following claims.

What is claimed is:

1. An interproximal squirt brush, comprising:

a solution container having a compressible solution chamber for containing a solution, and a nozzle head having an opening communicating with said compressible solution chamber, wherein said solution container comprises a container body defining said compressible solution chamber therein and having an opening portion communicating with said compressible solution chamber, wherein said nozzle head comprises a tubular nozzle base detachably mounted at said opening portion of said container body and a tubular brush holder coaxially extended from said nozzle base, wherein said brush holder has a guiding slot extended from a rear edge end of said brush holder; and a brush head, comprising:

an elongated brush arm having a brush portion and a retention portion connected to said nozzle head to hold said brush arm in position, wherein a dispensing channel is provided at said nozzle head adjacent to said retention portion of said brush arm to deliver said solution from said solution chamber to said brush portion of said brush arm through said nozzle head, wherein said retention portion of said brush arm is inserted into said brush holder to retain said brush head in position, wherein a length of said retention portion is longer than that of said brush holder, wherein said retention portion of said brush arm is inserted through said brush holder and an outward extending tail of said retention portion is bent towards said brush portion to form a U-shape structure at a rear end of said brush arm to securely hold said brush arm at the brush holder, wherein said outward extending tail of said retention portion of said brush arm is bent towards said brush portion and said outward extending tail of said retention portion is received in said guiding slot; and a brush member provided at said brush portion of said brush arm, thereby when a compression force is applied on said container body, said solution is released to deliver to said brush member through said dispensing channel of said nozzle head.

2. An interproximal squirt brush, comprising:

a solution container having a compressible solution chamber for containing a solution, and a nozzle head having an opening communicating with said compressible solution chamber, wherein said solution container comprises a container body defining said compressible solution chamber therein and having an opening portion communicating with said compressible solution chamber, wherein said nozzle head comprises a tubular nozzle base detachably mounted at said opening portion of said container body and a tubular brush holder coaxially extended from said nozzle base, wherein said brush holder has a guiding slot extended from a rear edge end of said brush holder, and a brush head, comprising:

an elongated brush arm having a brush portion and a retention portion connected to said nozzle head to hold said brush arm in position, wherein a dispensing channel is provided at said nozzle head adjacent to said retention portion of said brush arm to deliver said solution from said solution chamber to said brush portion of said brush arm through said nozzle head, wherein said retention portion of said brush arm is inserted into said brush holder to retain said brush head in position, wherein said retention portion of said brush arm is inserted into said opening of said brush holder and said dispensing channel is formed as a clearance between said retention portion of said brush arm and an inner wall of said brush holder of said nozzle head to allow said solution to pass through said dispensing channel towards said brush portion of said brush arm, wherein a length of said retention portion is longer than that of said brush holder, wherein said retention portion of said brush arm is inserted through said brush holder and an outward extending tail of said retention portion is bent towards said brush portion to form a U-shape structure at a rear end of said brush arm to securely hold said brush arm at the brush holder, wherein said outward extending tail of said retention portion of said brush arm is bent towards said brush portion and said outward extending tail of said retention portion is received in said guiding slot; and a brush member provided at said brush portion of said brush arm, thereby when a compression force is applied on said container body, said solution is released to deliver to said brush member through said dispensing channel of said nozzle head.

3. An interproximal squirt brush, comprising:

a solution container having a compressible solution chamber for containing a solution, and a nozzle head having an opening communicating with said compressible solution chamber, wherein said solution container comprises a container body defining said compressible solution chamber therein and having an opening portion communicating with said compressible solution chamber, wherein said nozzle head comprises a tubular nozzle base detachably mounted at said opening portion of said container body and a tubular brush holder coaxially extended from said nozzle base, wherein said solution container further comprises a sealing locker coaxially mounted to said container body to sealedly lock up said nozzle base at said opening portion of said container body, wherein said sealing locker comprises a locker ring fittingly mounted around said opening portion of said container body and a sealing rim coaxially and inwardly protruded from an edge of said locker ring to tightly and sealedly bias against said opening portion of said container body to hold said nozzle base in position for preventing said solution from leaking at said opening portion; and a brush head, comprising:

an elongated, brush arm having a brush portion and a retention portion connected to said nozzle head to hold said brush arm in position, wherein a dispensing channel is provided at said nozzle head adjacent to said retention portion of said brush arm to deliver said solution from said solution chamber to said brush portion of said brush arm through said nozzle head, wherein said retention portion of said brush arm is inserted into said brush holder to retain said brush head in position; and a brush member provided at said brush portion of said brush arm, thereby when a compression force is applied on said container body, said solution is released to deliver to said brush member through said dispensing channel of said nozzle head.

4. The interproximal squirt brush, as recited in claim 3, wherein said brush member comprises a plurality of wire bristles radially and spacedly extended along said brush portion of said brush arm for fitting between teeth and around a gum line of a user to perform a brushing and flossing action.

5. An interproximal squirt brush, comprising:

a solution container having a compressible solution chamber for containing a solution, and a nozzle head having an opening communicating with said compressible solution chamber, wherein said solution container comprises a container body defining said compressible solution chamber therein and having an opening portion communicating with said compressible solution chamber, wherein said nozzle head comprises a tubular nozzle base detachably mounted at said opening portion of said container body and a tubular brush holder coaxially extended from said nozzle base, wherein said solution container further comprises a sealing locker coaxially mounted to said container body to sealedly lock up said nozzle base at said opening portion of said container body, wherein said sealing locker comprises a locker ring fittingly mounted around said opening portion of said container body and a sealing rim coaxially and inwardly protruded from an edge of said locker ring to tightly and sealedly bias against said opening portion of said container body to hold said nozzle base in position for preventing said solution from leaking at said opening portion; and a brush head, comprising:

an elongated brush arm having a brush portion and a retention portion connected to said nozzle head to hold said brush arm in position, wherein a dispensing channel is provided at said nozzle head adjacent to said retention portion of said brush arm to deliver said solution from said solution chamber to said brush portion of said brush arm through said nozzle head, wherein said retention portion of said brush arm is inserted into said brush holder to retain said brush head in position, wherein said retention portion of said brush arm is inserted into said opening of said brush holder and said dispensing channel is formed as a clearance between said retention portion of said brush arm and an inner wall of said brush holder of said nozzle head to allow said solution to pass through said dispensing channel towards said brush portion of said brush arm; and a brush member provided at said brush portion of said brush arm, thereby when a compression force is applied on said container body, said solution is released to deliver to said brush member through said dispensing channel of said nozzle head.

6. An interproximal squirt brush, comprising:

a solution container having a compressible solution chamber for containing a solution, and a nozzle head having an opening communicating with said compressible solution chamber, wherein said solution container comprises a container body defining said compressible solution chamber therein and having an opening portion communicating with said compressible solution chamber, wherein said nozzle head comprises a tubular nozzle base detachably mounted at said opening portion of said container body and a tubular brush holder coaxially extended from said nozzle base, wherein said solution container further comprises a sealing locker coaxially mounted to said container body to sealedly lock up said nozzle base at said opening portion of said container body, wherein said sealing locker comprises a locker ring fittingly mounted around said opening portion of said container body and a sealing rim coaxially and inwardly protruded from an edge of said locker ring to tightly and sealedly bias against said opening portion of said container body to hold said nozzle base in position for preventing said solution from leaking at said opening portion; and a brush head, comprising:

an elongated brush arm having a brush portion and a retention portion connected to said nozzle head to hold said brush arm in position, wherein a dispensing channel is provided at said nozzle head adjacent to said retention portion of said brush arm to deliver said solution from said solution chamber to said brush portion of said brush arm through said nozzle head, wherein said retention portion of said brush arm is inserted into said brush holder to retain said brush head in position, wherein said retention portion of said brush arm is inserted into said opening of said brush holder and said dispensing channel is formed as a clearance between said retention portion of said brush arm and an inner wall of said brush holder of said nozzle head to allow said solution to pass through said dispensing channel towards said brush portion of said brush arm, wherein a length of said retention portion is longer than that of said brush holder, wherein said retention portion of said brush arm is inserted through said brush holder and an outward extending tail of said retention portion is bent towards said brush portion to form a U-shape structure at a rear end of said brush arm to securely hold said brush arm at the brush holder; and a brush member provided at said brush portion of said brush arm, thereby when a compression force is applied on said container body, said solution is released to deliver to said brush member through said dispensing channel of said nozzle head.

7. The interproximal squirt brush, as recited in claim 6, wherein said brush member comprises a plurality of wire bristles radially and spacedly extended along said brush portion of said brush arm for fitting between teeth and around a gum line of a user to perform a brushing and flossing action.

8. An interproximal squirt brush, comprising:

a solution container having a compressible solution chamber for containing a solution, and a nozzle head having an opening communicating with said compressible solution chamber, wherein said solution container comprises a container body defining said compressible solution chamber therein and having an opening portion communicating with said compressible solution chamber, wherein said nozzle head comprises a tubular nozzle base detachably mounted at said opening portion of said container body and a tubular brush holder coaxially extended from said nozzle base; and a brush head, comprising:

an elongated brush arm having a brush portion and a retention portion connected to said nozzle head to hold said brush arm in position, wherein a dispensing channel is provided at said nozzle head adjacent to said retention portion of said brush arm to deliver said solution from said solution chamber to said brush portion of said brush arm through said nozzle head, wherein said retention portion of said brush arm is inserted into said brush holder to retain said brush head in position, wherein a portion of said brush holder is flattened to press against said retention portion of said brush arm to hold said brush arm in position, wherein a clearance remained between said retention portion of brush arm and an inner wall of said brush holder of said nozzle head contributes said dispensing channel along said brush holder; and a brush member provided at said brush portion of said brush arm, thereby when a compression force is applied on said container body, said solution is released to deliver to said brush member through said dispensing channel of said nozzle head.

9. The interproximal squirt brush, as recited in claim 8, wherein said brush holder has a front portion to hold said retention portion of said brush arm in position and a rear portion extended from said nozzle base, wherein said front portion of said brush holder is inclinedly extended from said rear portion thereof such that said brush head is extended at an slanted position with respect to said solution container.

10. The interproximal squirt brush, as recited in claim 9, wherein said container body further comprises a piston member inserted in said container body to apply a compression force on said container body by pushing in said piston member for pressing said solution in said solution chamber to deliver to said brush member through said dispensing channel of said nozzle head.

11. The interproximal squirt brush, as recited in claim 10, wherein said brush member comprises a plurality of wire bristles radially and spacedly extended along said brush portion of said brush arm for fitting between teeth and around a gum line of a user to perform a brushing and flossing action.

12. The interproximal squirt brush, as recited in claim 9, wherein said brush member comprises a plurality of wire bristles radially and spacedly extended along said brush portion of said brush arm for fitting between teeth and around a gum line of a user to perform a brushing and flossing action.

13. The interproximal squirt brush, as recited in claim 8, wherein said container body further comprises a piston member inserted in said container body to apply a compression force on said container body by pushing in said piston member for pressing said solution in said solution chamber to deliver to said brush member through said dispensing channel of said nozzle head.

14. The interproximal squirt brush, as recited in claim 13, wherein said brush member comprises a plurality of wire bristles radially and spacedly extended along said brush portion of said brush arm for fitting between teeth and around a gum line of a user to perform a brushing and flossing action.

15. The interproximal squirt brush, as recited in claim 8, wherein said brush member comprises a plurality of wire bristles radially and spacedly extended along said brush portion of said brush arm for fitting between teeth and around a gum line of a user to perform a brushing and flossing action.

* * * * *